(12) United States Patent
Andrysek et al.

(10) Patent No.: US 7,087,090 B2
(45) Date of Patent: Aug. 8, 2006

(54) ARTIFICIAL KNEE JOINT

(75) Inventors: Jan Andrysek, Toronto (CA); Stephen Naumann, Toronto (CA); William L. Cleghorn, Toronto (CA)

(73) Assignee: Bloorview MacMillan Centre, Toronto (CA)

(*) Notice: Subject to any disclaimer, the term of this patent is extended or adjusted under 35 U.S.C. 154(b) by 0 days.

(21) Appl. No.: 10/990,488

(22) Filed: Nov. 18, 2004

(65) Prior Publication Data

US 2005/0149203 A1    Jul. 7, 2005

Related U.S. Application Data

(60) Provisional application No. 60/523,093, filed on Nov. 19, 2003.

(51) Int. Cl.
    *A61F 2/64* (2006.01)

(52) U.S. Cl. .......................... 623/44; 623/43

(58) Field of Classification Search ............... 623/44, 623/39, 43
    See application file for complete search history.

(56) References Cited

U.S. PATENT DOCUMENTS

| | | | |
|---|---|---|---|
| 62,731 A | 3/1867 | Carleton et al. | |
| 2,667,644 A * | 2/1954 | Johnson | 623/26 |
| 2,943,622 A * | 7/1960 | Nelson | 602/16 |
| 3,015,825 A | 1/1962 | Blatchford | |
| 3,546,712 A * | 12/1970 | Tarte | 623/41 |
| 3,806,958 A | 4/1974 | Gusev | |
| 3,823,424 A | 7/1974 | May | |
| 3,833,942 A | 9/1974 | Collins | |
| 3,863,274 A | 2/1975 | Glabiszewski | |
| 3,901,223 A | 8/1975 | May | |
| 3,982,279 A | 9/1976 | Valenti et al. | |
| 4,023,215 A | 5/1977 | Moore | |
| 4,064,569 A | 12/1977 | Campbell | |
| 4,135,254 A | 1/1979 | Weber et al. | |
| 4,145,766 A | 3/1979 | May | |
| 4,152,787 A | 5/1979 | Meggyesy | |
| 4,206,519 A | 6/1980 | Blatchford et al. | |
| 4,232,405 A | 11/1980 | Janovsky | |
| 4,310,932 A | 1/1982 | Nader et al. | |
| 4,370,761 A | 2/1983 | Serri | |
| 4,451,939 A | 6/1984 | Thompson | |
| 4,458,367 A | 7/1984 | May | |
| 4,549,318 A | 10/1985 | Takahama | |
| 4,614,518 A | 9/1986 | Lehneis et al. | |
| 4,685,926 A | 8/1987 | Haupt | |
| 4,685,927 A | 8/1987 | Haupt | |

(Continued)

FOREIGN PATENT DOCUMENTS

EP    0 325 347 A1    7/1989

(Continued)

OTHER PUBLICATIONS

C.W. Radcliffe (Bulletin of Prosthetics Research—Fall 1977 and—Spring 1979).

*Primary Examiner*—Corrine McDermott
*Assistant Examiner*—Thomas Sweet
(74) *Attorney, Agent, or Firm*—Miller Thomson LLP

(57) ABSTRACT

A prosthetic knee joint including stance-phase control means comprising lock or latch for holding the knee in a straight condition, and means determining the status of the latch, said status determining means defining a control axis located so that the lock or latch is activated when a load imposed on the joint passes through a line posterior to said axis, and is de-activated when the load passes through a line anterior to said axis.

10 Claims, 8 Drawing Sheets

U.S. PATENT DOCUMENTS

| | | |
|---|---|---|
| 4,723,539 A | 2/1988 | Townsend |
| 4,756,712 A | 7/1988 | Clover, Jr. |
| 4,756,713 A | 7/1988 | Cooper |
| 4,883,493 A | 11/1989 | Martel et al. |
| 4,911,709 A | 3/1990 | Marlow et al. |
| 4,997,449 A | 3/1991 | Prah et al. |
| 5,062,857 A | 11/1991 | Berringer et al. |
| 5,092,902 A | 3/1992 | Adams et al. |
| 5,171,325 A | 12/1992 | Aulie |
| 5,181,931 A | 1/1993 | van de Veen |
| 5,246,465 A | 9/1993 | Rinco et al. |
| 5,314,498 A | 5/1994 | Grammas |
| 5,376,135 A | 12/1994 | Aulie |
| 5,376,136 A | 12/1994 | Stenberg |
| 5,376,137 A | 12/1994 | Shorter et al. |
| 5,509,936 A | 4/1996 | Rappoport et al. |
| 5,545,232 A | 8/1996 | van de Veen |
| 5,571,205 A | 11/1996 | James |
| D383,542 S | 9/1997 | Wellershaus et al. |
| 5,704,945 A | 1/1998 | Wagner et al. |
| 5,704,946 A | 1/1998 | Greene |
| 5,746,774 A | 5/1998 | Kramer et al. |
| 5,755,813 A | 5/1998 | Krukenberg |
| 5,779,735 A | 7/1998 | Molino |
| 5,800,567 A | 9/1998 | Cooper et al. |
| D402,368 S | 12/1998 | Holzapfel |
| 5,888,237 A | 3/1999 | Shiraishi et al. |
| 5,893,891 A | 4/1999 | Zahedi |
| 5,895,429 A | 4/1999 | Cool et al. |
| 5,895,430 A | 4/1999 | O'Connor |
| 5,899,943 A | 5/1999 | Shiraishi et al. |
| 5,941,913 A | 8/1999 | Woolnough et al. |
| D425,621 S | 5/2000 | Swanson, Sr. |
| 6,086,616 A | 7/2000 | Okuda et al. |
| 6,139,586 A | 10/2000 | Wagner et al. |
| 6,159,248 A * | 12/2000 | Gramnas .................... 623/44 |
| D439,339 S | 3/2001 | Sawatzki |
| 6,517,585 B1 | 2/2003 | Zahedi et al. |

FOREIGN PATENT DOCUMENTS

| | | |
|---|---|---|
| EP | 0 358 056 B1 | 3/1990 |
| GB | 2 161 386 A | 1/1986 |
| GB | 2 192 544 A | 1/1988 |
| GB | 2334 891 A | 9/1999 |
| GB | 2338 653 A | 12/1999 |
| GB | 2367 753 A | 4/2002 |
| JP | 06225897 A | 8/1994 |
| RU | 2095037 C1 * | 11/1997 |
| WO | WO 92/18071 | 10/1992 |
| WO | WO 9641599 A1 * | 12/1996 |
| WO | WO 99/44547 | 9/1999 |
| WO | WO 01/17466 A2 | 3/2001 |
| WO | WO 01/72245 A2 | 10/2001 |

* cited by examiner a) Heel-stance  b) Mid-stance  c) Fore-foot loading

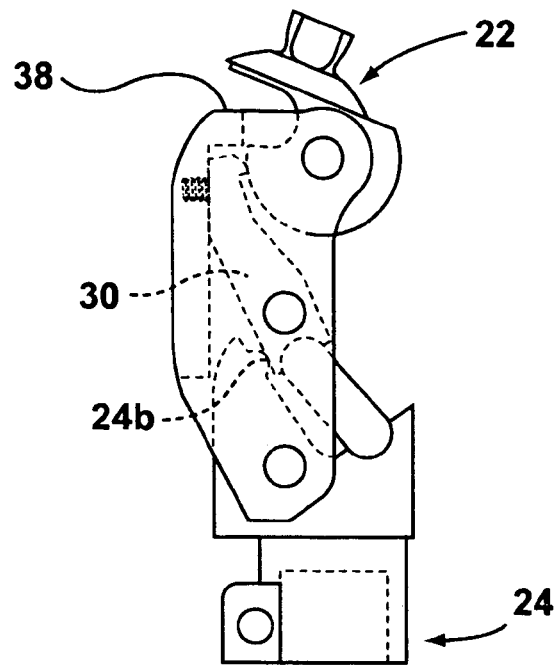
FIG. 11
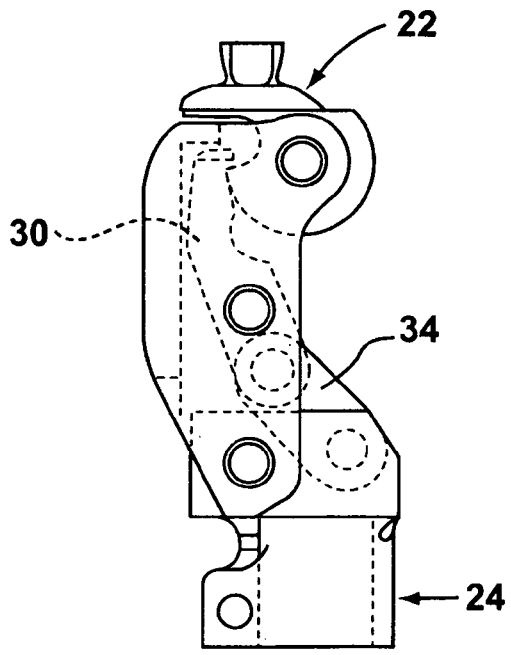 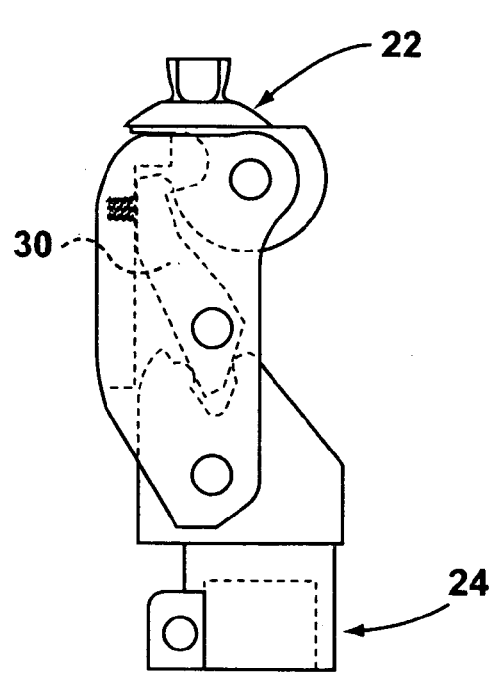
FIG. 12a FIG. 12b

ARTIFICIAL KNEE JOINT

CROSS-REFERENCE TO RELATED APPLICATIONS

This application claims benefits from U.S. provisional application Ser. No. 60/523,093 filed Nov. 19, 2003 which is incorporated herein by reference in its entirety.

FIELD OF THE INVENTION

This invention relates to artificial knee joints for use by human amputees or as orthotic devices.

BACKGROUND OF THE INVENTION

In general, an artificial (prosthetic) knee joint will be prescribed for a person with a through-knee (TK) or an above-knee (AK) amputation, i.e. a person without a knee joint, shank or foot. The ability for the knee to bend or articulate allows for activities such as sitting; it also allows the leg to swing during the swing-phase of gait (walking or running).

When standing or putting weight on the leg, as during the support-phase or stance-phase of the gait cycle it is undesirable for the prosthetic knee to bend uncontrollably as this will cause the amputee to fail. This is referred to as "stance-phase control". Amputees have some control during stance by the way they load the leg and how they use their remaining muscles at the hip. Alternatively, a prosthetist can align a prosthesis to be more or less stable by placing the knee joint axis behind the load bearing plane or load line. However, this tends not to produce ideal gait characteristics.

While many different designs have been proposed, the majority of prosthetic knee joints are designed to address the issue of stance-phase control, i.e. keeping the knee from articulating when the prosthesis is supposed to be providing support. A prosthetic knee joint may have a built-in "locking" mechanism for this purpose.

One type of lock is weight activated and provides the two conditions for when the knee is to be locked and when it should bend freely; that is, during weight-bearing and non-weight bearing respectively. However, this is not ideal because, for a natural gait and normal initiation of the swing-phase, the knee should begin to flex at the end of the stance-phase, even as the leg is still under load. It can be appreciated that this is not possible with a weight-activated knee since it remains locked as long as the prosthesis is under load.

A supplementary condition is needed in the control of the knee lock, so that during weight-bearing, the knee lock is inactive when the forefoot is loaded, or similarly, the knee lock is activated only when the rear of the foot is loaded. This is described in patents U.S. Pat. No. 3,015,825 and U.S. Pat. No. 5,704,945 and by C. W. Radcliffe (Bulletin of Prosthetics Research—Fall 1977 and—Spring 1979).

SUMMARY OF THE INVENTION

An object of the present invention is to provide an improved artificial knee joint. Although the invention is described with an intended application to the field of prosthetics, an adapted version of this knee mechanism may be used in orthotic applications.

According to the invention there is provided a prosthetic knee joint including stance phase control means comprising lock means for holding the knee in a straight condition and means determining the status of the lock means. The status determining means defines a control axis located so that the lock means is activated when a load imposed on the joint in use passes through a line posterior to the axis, and is deactivated when the load passes through a line anterior to the axis.

Preferably, the joint includes a main body and upper and lower coupling elements for attachment to respective upper and lower parts of a leg in which the joint is to be used. The upper coupling element is pivotally mounted to the main body for defining a knee axis and the lower coupling element is pivotally mounted to the main body for defining the control axis. The lock means acts between the upper and lower coupling elements for restraining the upper coupling element against movement about the knee axis when the load imposed on the joint passes through a line posterior to the control axis and to release the upper coupling element for movement about the knee axis when the load passes through a line anterior to the control axis.

The lock means preferably includes a latch member pivotally coupled to the main body of the knee joint about a lock axis intermediate upper and lower ends of the member for movement between an activated position and a deactivated position. An upper end portion of the latch member and the upper coupling element are shaped to define inter-engageable latch formations arranged so that the upper coupling element is restrained against movement about the knee axis when the latch member is in the activated position. The lower coupling element includes first and second portions oppositely engageable with a lower end region of the latch member for displacing the latch member about the lock axis between said activated position and said deactivated position in response to pivotal movement of the lower coupling element with respect to the main body about the control axis.

In summary, the invention incorporates two main features, one relating to the method of how the knee locks (means of locking) while the other relates to how the lock is controlled (means of control of lock). The locking means may generally be described as a latch, plunger or lock. The status of the lock (or latch), that is whether it is engaged or disengaged, is determined by means of a control axis. The acting torque at this control axis, which is a function of the loading of the prosthesis, is transmitted via a novel mechanical system to engage and disengage the lock. The use of a control axis with a latch type of lock is believed to be novel.

BRIEF DESCRIPTION OF THE DRAWINGS

In order that the invention may be more clearly understood, reference will now be made to the accompanying drawings which illustrate particular preferred embodiments of the invention by way of example, and in which:

FIG. 11 is a view showing an embodiment in which the knee joint incorporates a cushioning feature;

FIGS. 12a) and 12b) show further alternative embodiments; and,

DESCRIPTION OF PREFERRED EMBODIMENTS

Figure 1:
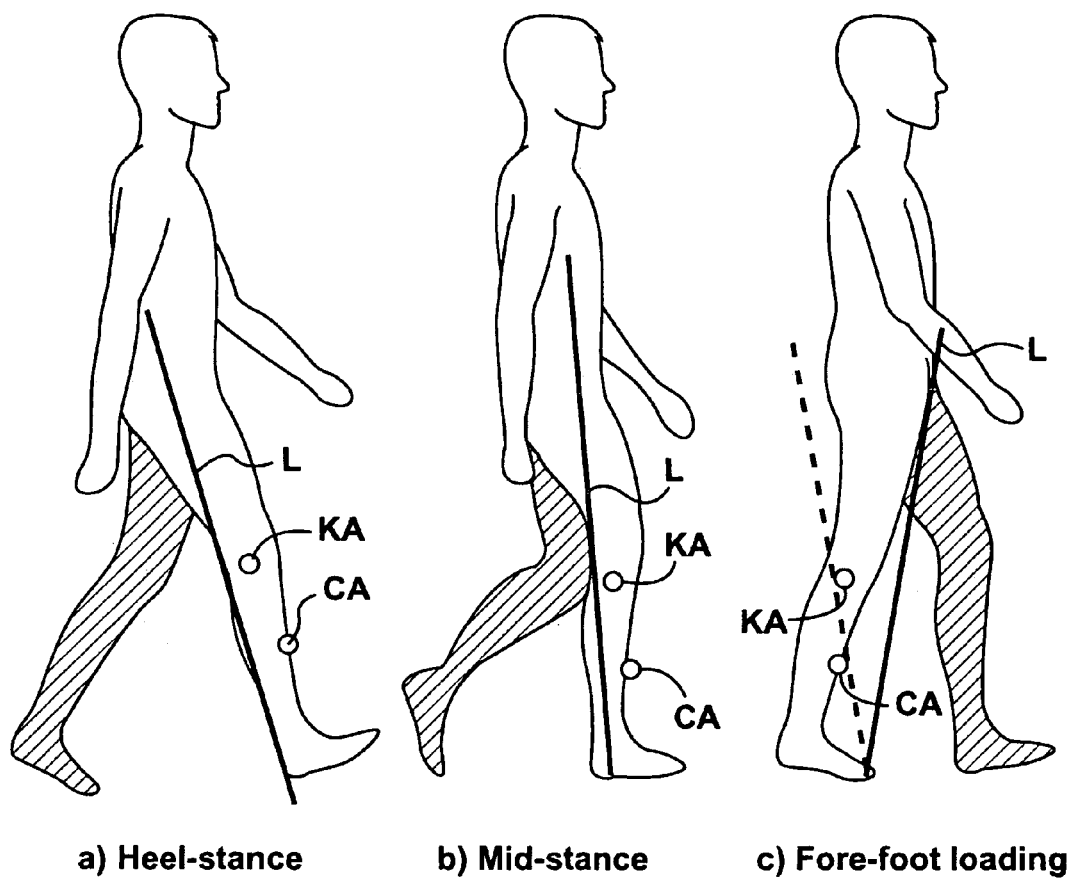
FIG. 1 comprises three diagrams denoted a), b) and c) that illustrate use of a control axis to control an artificial knee joint.
Figure 2A:
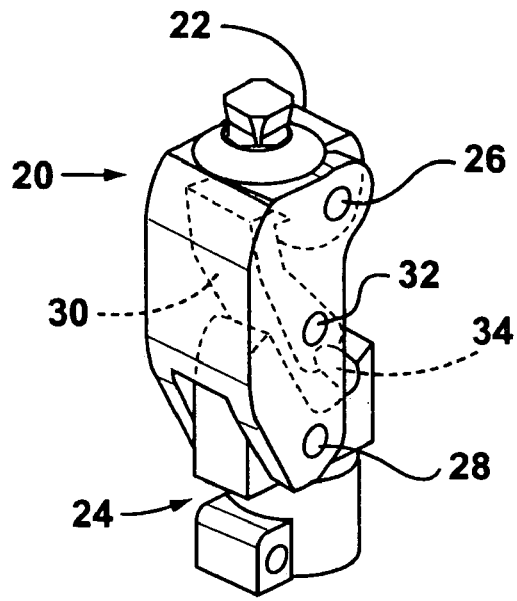
FIG. 2 comprises four schematic perspective views denoted a) to d), illustrating the knee joint of the invention.
Figure 2B:
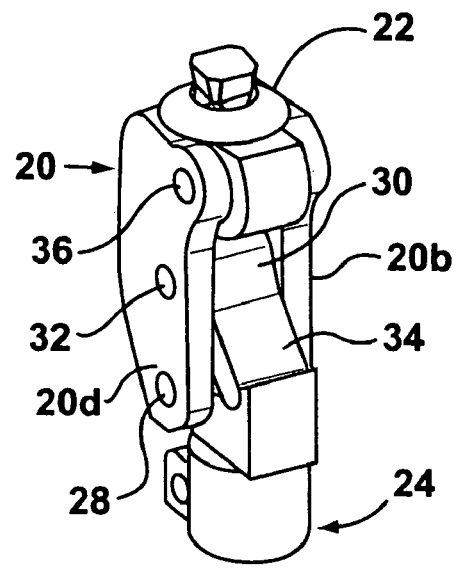
Figure 2C:
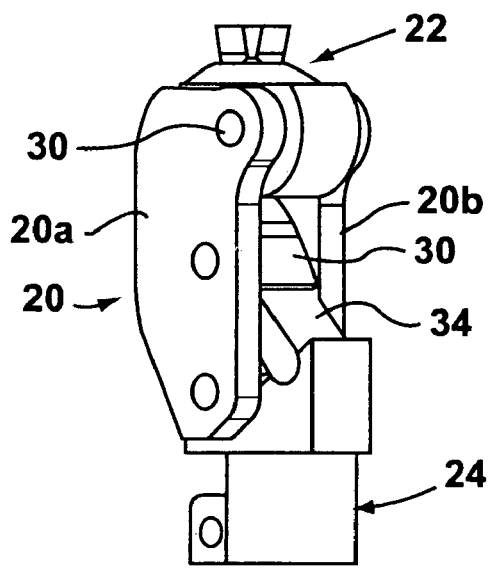
Figure 2D:
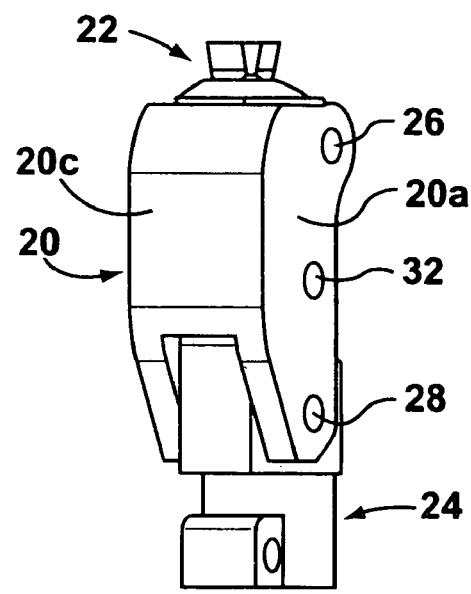

Reference will first be made to FIG. 1 is describing control of an artificial knee joint in accordance with the teachings of Radcliffe supra. As noted previously, the knee should be controlled so that during weight bearing, the knee lock is inactive when the fore foot is loaded, or similarly, the knee lock is activated only when the rear and/or mid-region of the foot is loaded. In the three diagrams that make up FIG. 1, a load line through the leg is denoted L. The pivot axis of the knee (knee axis) is denoted KA and a control axis is denoted CA. The knee axis KA and control axis CA are shown as white dots with CA below and in front of KA.

In diagram a) the knee would normally collapse since the load line L passes behind KA and causes a flexion moment at KA. However, the control is such that as long as there is a flexion moment at CA, a lock is activated at KA. The person rolls over the foot until the toe is loaded, (diagram c)), at which point the person will apply a flexion moment at the hip via their muscles. That will cause the load line to pass posterior of KA. Since at this time the load line is anterior of CA, thus causing an extension moment about CA and deactivating the lock, the knee is able to bend and swing-phase can be initiated.

Figure 3:
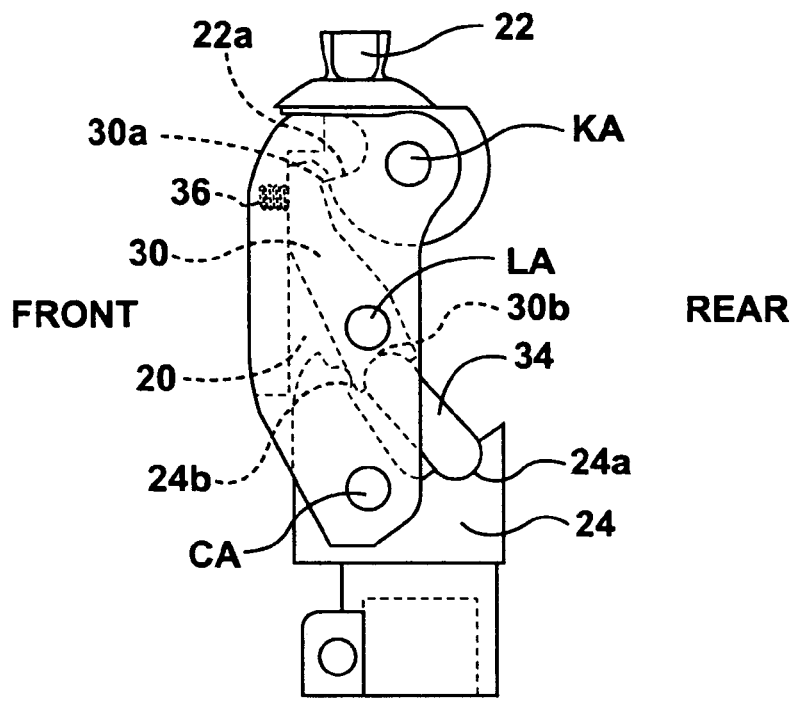
FIG. 3 is a schematic illustration of a knee joint in accordance with the invention.

Reference will now be made to FIG. 2 in conjunction with FIG. 3 is describing the knee joint provided by the invention. Referring primarily to FIG. 2, the knee joint has a main body or housing 20 that has a generally channel-shaped configuration, comprising two side members 20a, 20b and a front member 20c. Respective upper and lower coupling elements 22 and 24 are pivotally mounted between upper and lower portions respectively of the housing side members 20a and 20b. Pivot pins for the coupling elements are denoted 26 and 28 respectively. As best seen in FIG. 3, the upper pivot pin 26 defines the knee axis KA of the joint while the lower pivot pin 28 defines the control axis CA.

Figure 13:
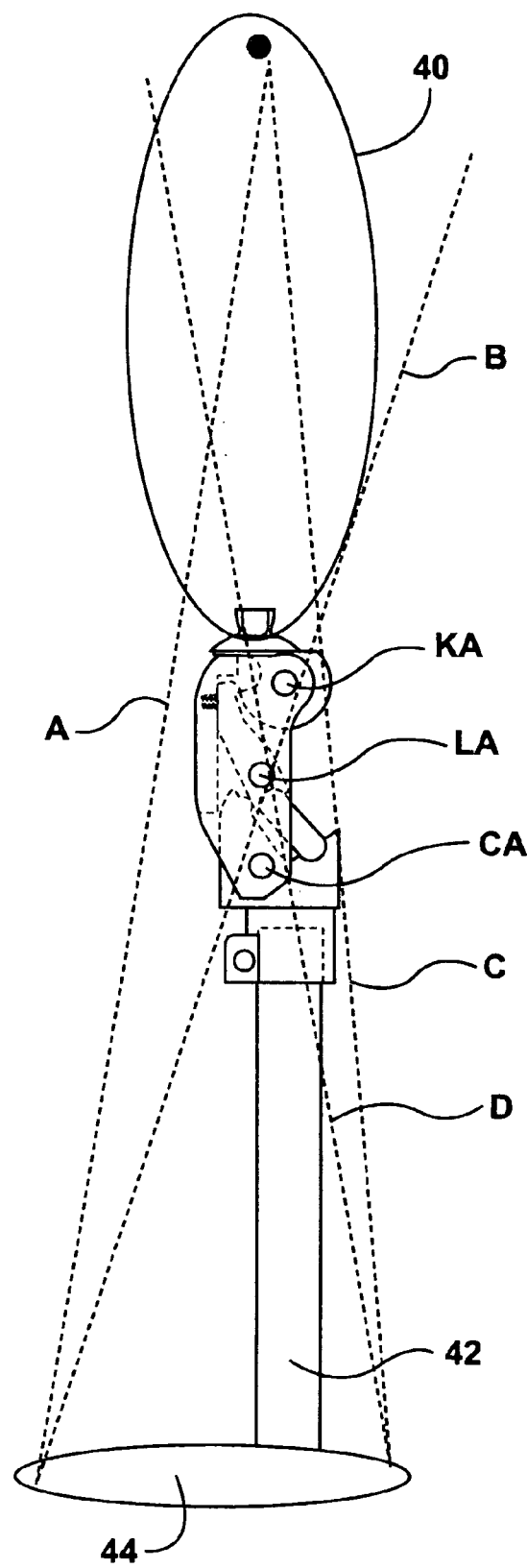
FIG. 13 is an overall schematic illustration of the knee joint of the invention in use.

The two coupling elements 22, 24 are designed as is conventional in the art to permit coupling of the artificial knee between the thigh bone (femur) of the patient and, typically, a shank of an artificial leg, for example as shown in FIG. 13. Precise details of the design of the coupling elements have not been shown and are conventional.

Also pivotally coupled between the side members 20a and 20b of the main body 20 of the artificial knee is a latch member 30, the profile shape of which is best seen in FIG. 3. A pivot pin for that member is indicated at 32 and extends parallel to the pivot pins 26, 28 for the top and bottom coupling elements. Pin 32 defines a lock axis LA.

Latch member 30 is shaped at its upper end to include a generally hook-shaped portion 30a that engages over a corresponding ledge 22a formed within a recessed portion of the top coupling element 22 inside the housing 20. The hook 30a and the ledge 22a co-operate to provide a locking function at appropriate times during the gait of a patient fitted with the artificial knee, as will be described later.

Referring back to FIG. 3, a force transfer link 34 extends between an upper portion of the bottom coupling element 24 and a bottom end portion of the latch member 30. The force transfer link 34 has upper and lower ends that are convexly curved as seen from the side and that are received in complimentary seats 30b in member 30 and 24a in the lower coupling element 24. These seats allow the force transfer link to oscillate back and forth as the patient walks.

The lower coupling element 24 is also shaped to define a force transfer contact element 24b that bears against the lower front edge of the lock member 30 for unlocking of the knee lock during walking. As will become apparent from the description which follows, the design of the artificial knee provided by the invention results in the knee lock being automatically activated and deactivated during walking, depending on how the patient's leg is loaded.

Figure 4:
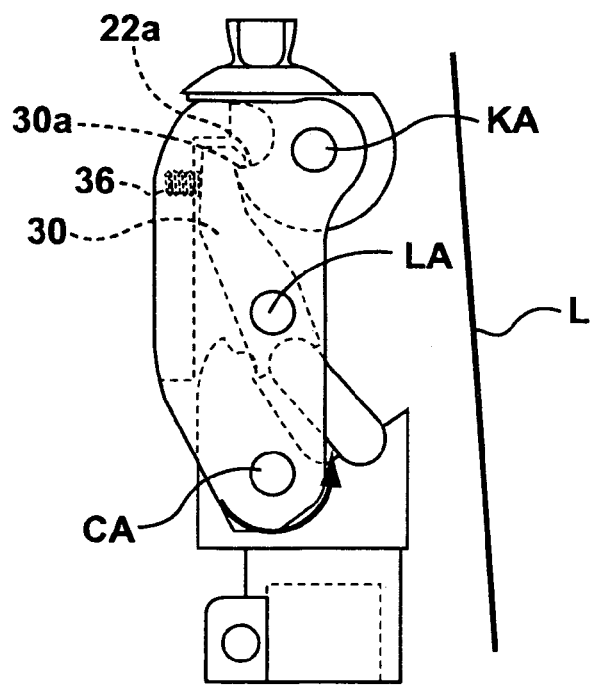
FIG. 4 is a view similar to FIG. 3 showing lock activation.
Figure 5:
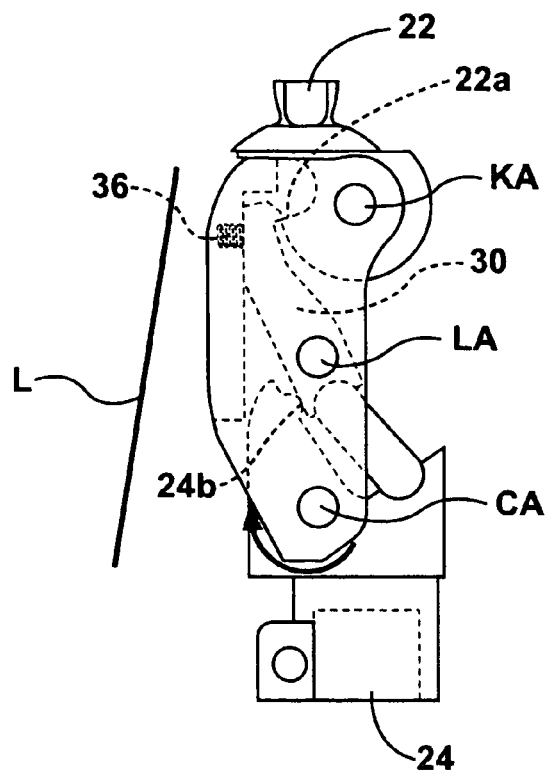
FIGS. 5 and 6 are views similar to FIG. 4 illustrating deactivation of the lock.

Reference will now be made to FIGS. 4 and 5 of the drawings respectively in describing locking and unlocking of the joint.

Lock Activation (Engagement):

Referring to FIG. 4, a load line L that passes posterior of control axis (CA), as is the case during heel-strike, will generate a counter-clockwise (CCW) moment about CA acting on the bottom coupling element 24 relative to the main body 20. Via the force transfer link 34, this applies a force on the bottom of the latch member 30 that will tend to rotate it clockwise (CW) about the lock axis (LA) relative to the main body 20 and engage it with the top coupling element 22 thus preventing the CW rotation of the element 22 relative to the main body 20. As the heel-load increases the locking force at the lock link 30 also increases thus ensuring the lock will remain engaged.

Figure 6:
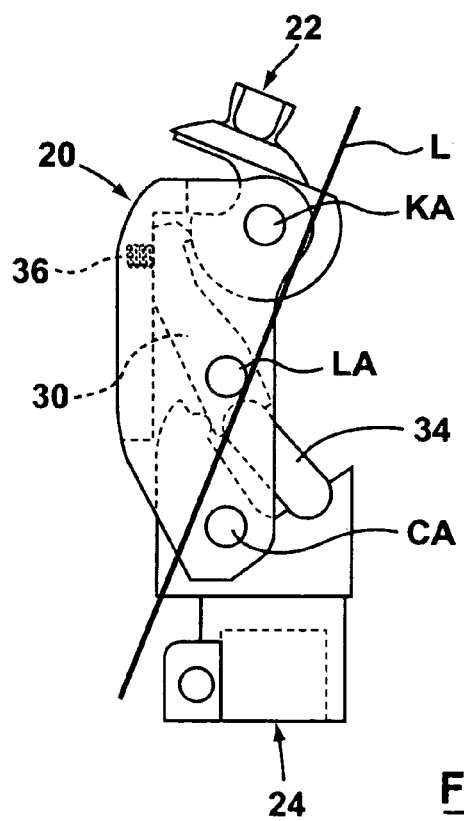

Lock Deactivation (Disengagement):

Referring to FIG. 5, when the load line passes anterior of CA, it generates a CW moment on the bottom coupling element 24 relative to the main body 20 about CA. Via the force transfer contact element 24b a force is applied on the bottom of the latch member 30 that will tend to rotate it CCW about LA relative to the main body 20 and disengage it from the locked position. This occurs when the prosthesis is loaded at the toe (FIG. 5). At this time if the amputee applies a hip flexion moment such that the load passes posterior of the knee axis (KA), the knee will tend to bend about that axis, as illustrated in FIG. 6.

Figure 7:
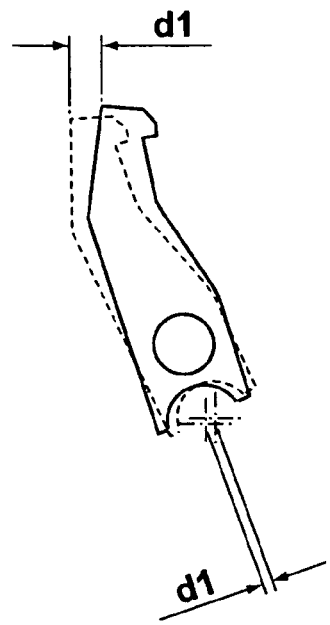
FIG. 7 is a view showing displacement of the lock.

It should be noted that during the, activation and deactivation of the lock, the bottom coupling element 24 will rotate a small amount relative to the main body 20, as a result of the moment applied. It is desirable to minimize the amount of this rotation which would otherwise make the prosthesis feel "wobbly" to the amputee. By virtue of the location of the lock axis LA closer to the lower end than to the upper end of the latch member, the joint amplifies rotation about CA of the bottom coupling element 24 relative to the main body 20 to achieve increased displacement of the upper end of the latch member 30 about LA and therefore a substantial engagement of the latch member. In FIG. 7, it can be seen that for a small input displacement d2, a much larger output (lock) displacement d1 is achieved. This allows rotation of the bottom coupling element to be minimized, reducing any "wobbly" feeling.

Figure 8:
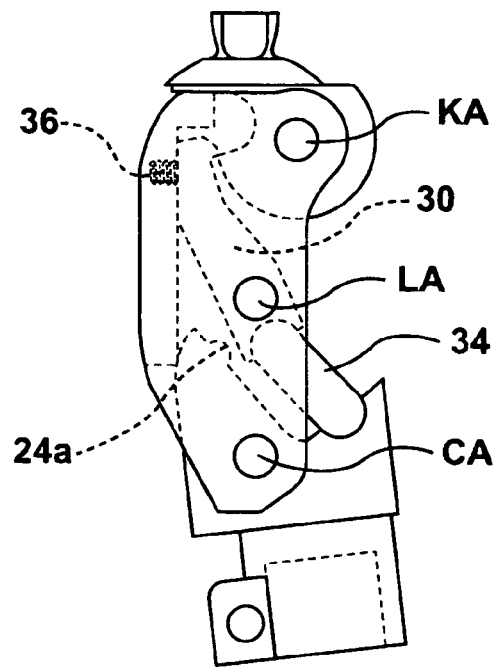
FIG. 8 is another view illustrating stance flexion.
Figure 9:
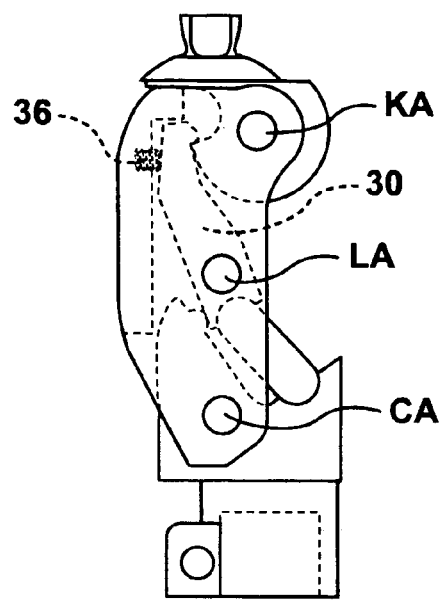
FIG. 9 is a view showing a spring in the artificial knee joint for biasing the lock into the engaged position.

Stance Flexion:

The force transfer link 30 may be made from a resilient material, so that it will compress (decrease in length) as a CCW moment is generated at the bottom coupling element 24 about CA and along with it 5 to 20 degrees CCW rotation of the bottom coupling element 24 relative to the main body 20 as shown in FIG. 8. This slight rotation, or knee bend, occurring at heel-strike, provides shock-absorption and more natural gait.

Optional Features:

The drawings show at 36 an optional spring that can be used to bias the latch member 30 into the engaged position. If a spring is used to bias the member to the engaged position, the knee will be locked by default whenever the knee is fully extended, thus providing very safe support to the amputee, and will only unlock if the prosthesis is loaded at the toe and the amputee concurrently applies a hip flexion moment by using his/her hip muscles. This enables the knee to bend at the initiation of the swing-phase. Alternatively, a spring can bias the latch member 30 to the disengaged position.

Figure 10A:
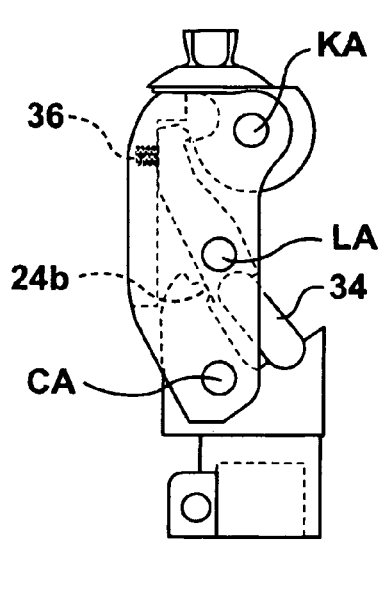
FIG. 10 comprises three views denoted a), b) and c) illustrating an alternative embodiment in which a spring biases the lock to the disengaged position.
Figure 10B:
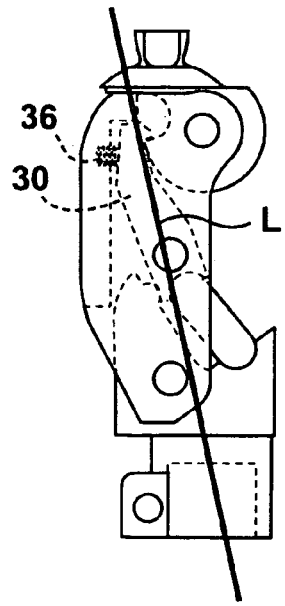
Figure 10C:
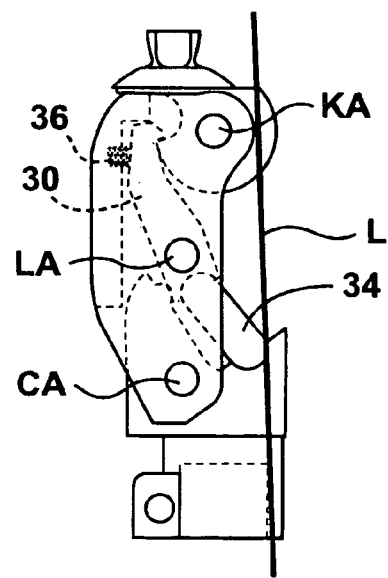

The absence of a spring bias may allow the knee lock to remain disengaged even at heel-strike unless the amputee applies a hip extension moment just as the foot contacts the ground at heel-strike. With this small hip extension moment the knee lock will engage thus providing support. FIG. 10 shows the knee lock disengaged by default and engageable voluntarily by the amputee. Diagram b) depicts a load line required to engage the lock. Once the knee lock is engaged, the amputee no longer needs to apply a hip extension moment to stabilize the leg—diagram c).

As shown in FIG. 11, an extension stop 38 including a soft bumper may be provided between the main body 20 and top coupling element 22 to cushion terminal impact at the end of the swing-phase.

A variation of this mechanism can be seen in FIG. 12*a*), in which the force transfer link 34 is pivotally coupled at its respective ends to the latch member 30 and the lower coupling element 24 or otherwise constrained so as to be capable of transferring extension moments as well as flexion moments, thus both engaging and disengaging the knee lock.

Another variation of the mechanism can be seen in FIG. 12*b*), in which the force transfer link 34 is omitted and the lower coupling element 24 applies force directly on the bottom of the latch member 30 to cause lock engagement.

The control of the knee lock is described further in Table 1 and shown in FIG. 13, in which a patient's thigh is schematically shown at 40 and an artificial shank and foot at 42 and 44 respectively.

TABLE 1

| | Load line anterior of KA | Load line posterior of KA |
|---|---|---|
| Load line anterior of CA | Knee stable and knee lock disengaged | Knee bends and knee lock disengaged |
| Load line posterior of CA | Knee stable and knee lock engaged | Knee will only be stable if the lock was initially engaged If the lock was not initially engaged, it may or may not engage (indeterminate) depending on whether at the instant of engagement the top link is in a fully extended position (i.e. knee is fully extended) |

In FIG. 13, the dotted lines denoted A to D represent the load lines noted below and correspond to the following knee control conditions:

A: No hip flexion moment applied by amputee and foot loaded at toe—load line anterior of KA—knee is inherently stable; lock tends not to engage.

B: Hip flexion moment applied by amputee and foot loaded at toe—load line posterior of KA and anterior of CA—knee will flex; lock tending to disengage.

C: No hip flexion moment applied by amputee and foot loaded at heel—load line posterior of both axis—knee will bend if lock is not engaged; knee will be locked if lock is initially engaged; lock tends toward engagement.

D: A small hip flexion moment is applied by amputee and foot loaded at heel—load line posterior of CA and anterior of KA—knee will not bend as it is inherently stable; lock tends towards engagement.

In summary, it should be noted that the preceding description relates to particular preferred embodiments of the invention only and that modifications may be made within the broad scope of the invention. Some of those modifications have been indicated previously and others will be apparent to a person skilled in the art.

The invention claimed is:

1. An artificial knee joint including a means for stance-phase control comprising a latch member for holding the knee in a straight condition, and a means for determining the status of the latch member, said status determining means defining a control axis located so that the latch member is activated when a load imposed on the joint in use passes through a line posterior to said control axis, and is de-activated when the load passes through a line anterior to said control axis.

2. A knee joint as claimed in claim 1, comprising a main body and upper and lower coupling elements for attachment to respective upper and lower parts of a leg in which the joint is to be used, said upper coupling element being pivotally mounted to the main body for defining a knee axis and said lower coupling element being pivotally mounted to the main body for defining said control axis, the latch member acting between said upper and lower coupling elements for restraining the upper coupling element against movement about said knee axis when the load imposed on the joint passes through the line posterior to said control axis, and to release said upper coupling element for movement about said knee axis when the load passes through the line anterior to said control axis in use.

3. An artificial knee joint, including a means for stance phase control comprising:
   (a) a latch member for holding the knee in a straight condition;
   (b) a means for determining the status of the latch member, said status determining means defining a control axis located so that the latch member is activated when a load imposed on the joint in use passes through a line posterior to said control axis, and is de-activated when the load passes through a line anterior to said control axis;
   (c) a main body and upper and lower coupling elements for attachment to respective upper and lower parts of a leg in which the joint is to be used, said upper coupling element being pivotally mounted to the main body for defining a knee axis and said lower coupling element being pivotally mounted to the main body for defining said control axis, the latch member acting between the upper and lower coupling elements and is pivotally coupled to said main body about a lock axis intermediate upper and lower ends of the latch member for movement between an activated position and a deactivated position; and
   (d) an upper end portion of the latch member and said upper coupling element being shaped to define interengageable latch formations arranged so that said upper coupling element is restrained against movement about said knee axis when the latch member is in said activated position and when the load imposed on the ioint passes through the line posterior to said control axis, wherein the lower coupling element includes first and second portions oppositely engageable with a lower end region of said latch member for displacing the latch member about said lock axis between said activated position and said deactivated position in response to pivotal movement of the lower coupling element with respect to the main body about said control axis when the load passes through the line posterior or anterior to said control axis in use.

4. A knee joint as claimed in claim 3, wherein said lock axis is located closer to the lower end of the latch member than to the upper end so that angular movement of the lower end of the latch member about said lock axis results in amplified displacement of the upper end of the latch member about said axis.

5. A knee joint as claimed in claim 3, wherein said first portion of the lower coupling element comprises a formation on said lower coupling element that defines a force transfer contact point positioned for contact with an anterior side of said latch member, and wherein the second portion of the lower coupling element comprises a force transfer link extending between a portion of said lower coupling element at a posterior side of the latch member and a lower end portion of the latch member, said force transfer link being received in respective radiused seats in the respective coupling element and latch member for permitting the force transfer link to cause said latch member to oscillate about said lock axis as a load imposed on the joint passes within locations posteriorly and anteriorly of the control axis when the knee joint is in use.

6. A knee joint as claimed in claim 5, wherein said force transfer link is resiliently compressible in a lengthwise direction to provide shock absorption knee joint is in use.

7. An artificial knee joint as claimed in claim 3, wherein the means for controlling the stance phase further comprises an adjustable force transfer linkage assembly having a first end with a biased compensation element adapted to engage the latch member, and a second end having an elastomeric portion adapted to engage the lower coupling element wherein the activation of the biased compensation element adjusts the length of the adjustable force transfer linkage assembly.

8. An artificial knee joint as claimed in claim 3, wherein the biased compensation element is wedge shaped.

9. An artificial knee ioint as claimed in claim 8, wherein the wedge shaped compensation element is activated by a spring.

10. An artificial knee joint including a means for controlling a stance-phase comprising
    (a) a latch member for holding the knee in a straight condition;
    (b) a means for determining the status of the latch member, said status determining means defining a control axis located so that the latch member is activated when a load imposed on the ioint in use passes through a line posterior to said control axis, and is de-activated when the load passes through a line anterior to said control axis; and
    (c) a main body and upper and lower coupling elements for attachment to respective upper and lower parts of a leg in which the ioint is to be used, said upper coupling element being pivotally mounted to the main body for defining a knee axis and said lower coupling element being pivotally mounted to the main body for defining said control axis, the latch member acting between said upper and lower coupling elements for restraining the upper coupling element against movement about said knee axis when the load imposed on the ioint passes through a line posterior to said control axis, and to release said upper coupling element for movement about said knee axis when the load passes through a line anterior to said control axis in use, wherein the main body and upper coupling element have respective contact surfaces that define a rest position of the joint, and wherein the joint further comprises a resilient cushioning element cushioning contact of said surfaces with one another.

* * * * *